United States Patent [19]

Guggenheim et al.

[11] 4,353,891
[45] Oct. 12, 1982

[54] MUTANASE

[76] Inventors: Bernhard Guggenheim, 25 Alfred-Escherstrasse; Hans-Rudolf Muhlemann, 8 Beustweg, both of Zurich, Switzerland

[21] Appl. No.: 190,621

[22] Filed: Oct. 19, 1971

[30] Foreign Application Priority Data

Oct. 26, 1970 [GB] United Kingdom ............... 50712/70

[51] Int. Cl.$^3$ .......................... A61K 7/28; C12N 9/24
[52] U.S. Cl. ...................... 424/50; 424/94; 435/200; 435/885
[58] Field of Search ............... 195/62, 65, 66; 424/50, 424/94

[56] References Cited

U.S. PATENT DOCUMENTS 3,622,661 11/1971 King ............................... 424/94 X
3,686,393 8/1972 Woodruff ............................ 424/50

*Primary Examiner*—Lionel M. Shapiro
*Attorney, Agent, or Firm*—Fidelman, Wolffe & Waldron

[57] ABSTRACT

This invention relates to a class of α1,3 glucan 3-glucanohydrolase named mutanase. The α1,3 glucosidic bonded polysaccharides hydrolyzed by these enzymes, herein termed mutan, forms part of the matrix material of dental plaque.

Mutanase may be produced by culturing microorganisms such as, Trichoderma, Penicillium, or Streptococcus on a glucan characterized by at least 50% alpha -1, 3 glucosidic bonds.

Mutanase containing compositions are adapted for disintegrating in vivo essential structural components of dental plaque.

8 Claims, 3 Drawing Figures

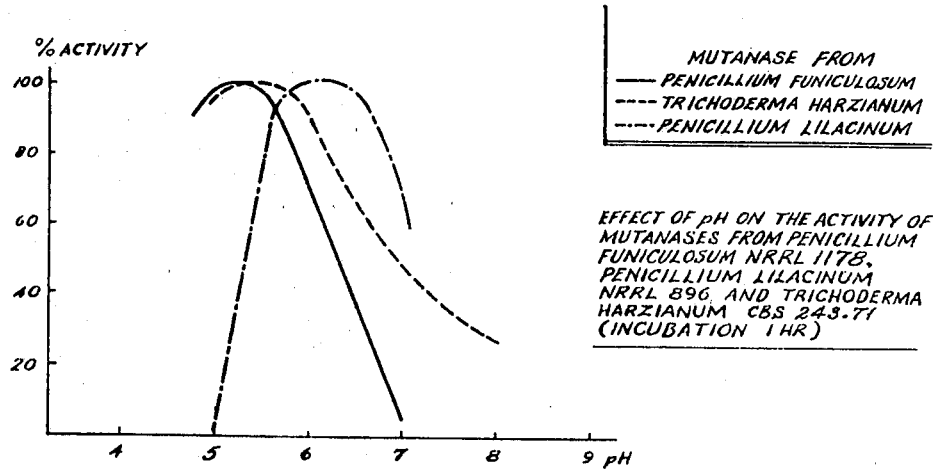

EFFECT OF pH ON THE ACTIVITY OF MUTANASES FROM PENICILLIUM FUNICULOSUM NRRL 1178, PENICILLIUM LILACINUM NRRL 896 AND TRICHODERMA HARZIANUM CBS 243.71 (INCUBATION 1 HR)

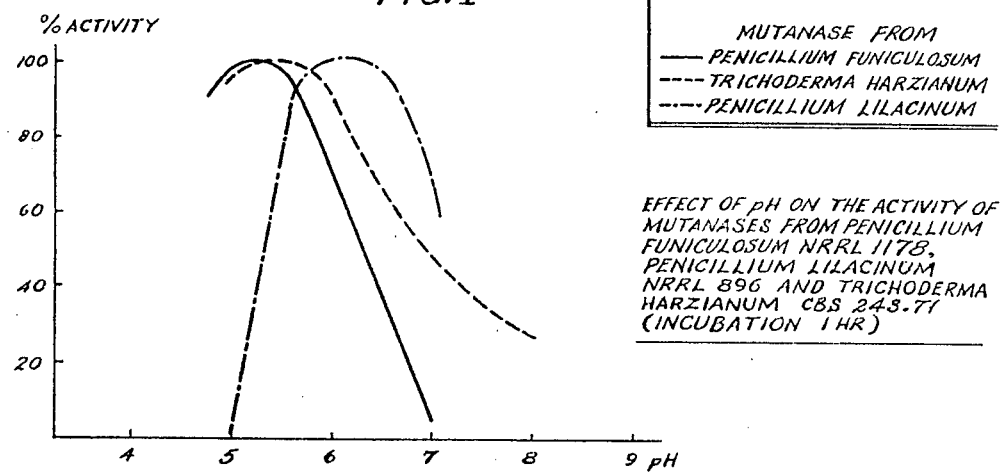

FIG.1

MUTANASE FROM
— PENICILLIUM FUNICULOSUM
---- TRICHODERMA HARZIANUM
—·— PENICILLIUM LILACINUM

EFFECT OF pH ON THE ACTIVITY OF MUTANASES FROM PENICILLIUM FUNICULOSUM NRRL 1178, PENICILLIUM LILACINUM NRRL 896 AND TRICHODERMA HARZIANUM CBS 243.71 (INCUBATION 1 HR)

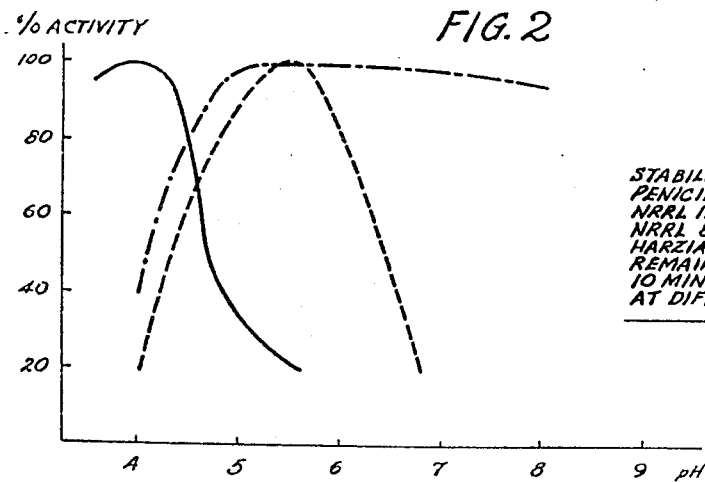

FIG.2

STABILITY OF MUTANASES FROM PENICILLIUM FUNICULOSUM NRRL 1178, PENICILLIUM LILACINUM NRRL 896 AND TRICHODERMA HARZIANUM CBS 243.71 REMAINING ACTIVITY AFTER 10 MIN. INCUBATION AT 50°C AT DIFFERENT pH.

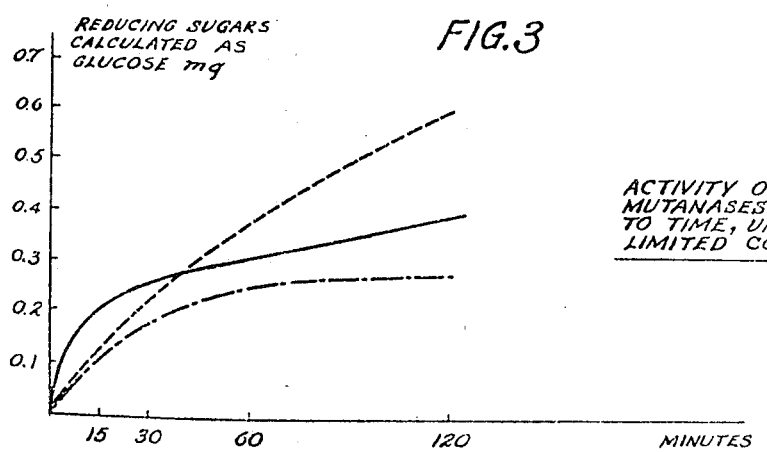

FIG.3

ACTIVITY OF DIFFERENT MUTANASES IN RELATION TO TIME, UNDER SUBSTRATE LIMITED CONDITIONS.

MUTANASE

This invention relates to the treatment of dental plaque and more particularly relates to an enzyme capable of attacking plaque.

Dentists and general public alike have long been aware that presence of the surface deposit on teeth known as dental plaque is undesirable. Plaque is believed to be related to the occurrence of caries and to the formation of cavities beneath the plaque. Dental plaque is also believed to be associated with early periodontal disease, gum irritation, and gingival diseases. A long sought after goal has been for ways to prevent formation of dental plaque and ways to remove dental plaque from teeth. Routine practice in a dental check-up is for the dentist or dental assistant to remove the plaque or tartar by scraping same from the teeth.

Numerous investigators have delved into the chemical nature of dental plaque and have reported that the plaque contains approximately 70% bacteria (by volume), with streptococci predominant among these bacteria. The remaining 30% includes extracellular bacterial products, glycoproteins from oral fluids, and substantial quantities of polysaccharide. The polysaccharide appears to be the insoluble skeleton or matrix which holds the plaque together. It is believed that these matrix polysaccharides are of bacterial origin, being formed from dietary carbohydrates by some of the bacteria regularly present in plaque, predominately by streptococci from dietary sucrose.

Certainly, polysaccharides are known to be produced by many strains of microorganisms e.g. dextran. Indeed some literature has identified the polysaccharide in dental plaque with dextran, to alpha (1→6) linked glucan or to levan, beta-(2→6) linked fructan and such identification led to suggestions to attack dental plaque in situ by treatment with a dextranase (as for example British Pat. No. 1,202,629). Some experimental support exists for believing that dextranase might attack plaque. In Vitro studies showed that the soluble dextrans were readily cleaved by dextranase, unfortunately, insoluble polysaccharides were attacked to only a limited extent. However, synthesis of an insoluble polysaccharide by a polysaccharide synthesizing microorganism containing system could be prevented when dextranase was added. All in all, use of dextranase in oral preparations for the purpose of removing plaque or even for reducing plaque formation has not been an unqualified success to date.

Guggenheim and Schroeder (Helv. odont. Acta 11, 131-182, 1967) observed that cariogenic streptococci (*Strep. mutans*) in sucrose-containing media synthesize water soluble dextran and insoluble glucan. Besides the α-(1→6) links, α-(1→3) bonds were also detected. The nature of this investigation was only qualitative. The insoluble glucan was fibrillar. By its insolubility in water, this glucan is clearly distinguishable from dextran, which is water soluble. Furthermore, the insoluble glucan is not attacked by dextranases inherent to some bacteria in dental plaque (Wood, Arch. oral. Biol. 14, 161-168, 1967) and is not solubilized and washed out by oral fluid in vivo. This glucan is sticky and has a great affinity for enamel, thus enhancing the colonization of streptococci on hard surfaces, e.g., on dental enamel or on artificial dentures etc.

The isolation of insoluble glucans from streptococci grown in sucrose-containing cultures is difficult. Therefore, the enzymes responsible for their synthesis were isolated (Guggenheim and Newbrun, Helv. odont. Acta 13, 84-87, 1969). A number of glucosyltransferases were isolated, and insoluble glucans were cell-free synthesized in vitro. The structural analysis of these glucans is an essential basis for this invention.

The critical ingredient in dental plaque is now believed to be polysaccharides with alpha 1,3-glucosidic bonds. These polysaccharides are quite insoluble in water. They are not attacked by dextranase. Their presence in dental plaque appears to be important for the resistance of plaque to attack by dextranase. This polysaccharide material has been termed mutan, and the enzymes which attack these polysaccharides (i.e. mutan) are identified as mutanase. Some of the laboratory work on mutan and mutanase has been published, reference hereby being made thereto for further elucidation concerning this invention: "Enzymatic Hydrolysis and Structure of Water-Insoluble Glucan Produced by Glucosyltransferases from a Strain of Streptococcus Mutans". Helv. odont. Acta 14, Supplementum V, 89-108, 1970.

The structural analyses were performed by a controlled Smith Degradation (Goldstein et al in: Methods in Carbohydrate Chemistry, Vol. V, General Polysaccharides, New York/London, p. 361-370, 1965) and by methylation with subsequent hydrolysis (Sanfad and Carrad, Biochemistry 5, 1508, 1965).

The results are summarized in the following tables:

(a) Smith Degradation

| Mode of Linkage | Mol % ± S |
|---|---|
| Gp- (1 or 6) -Gp-(1 3) -Gp-(1 6) | 15.9 ± 0.5 |
| or 3) -Gp-(1 | 84.1 ± 0.5 |

Gp = Glucopyranose, N = 6

(b) Methylation

| Mode of Linkage | mol % |
|---|---|
| Gp-(1 | 3% |
| 6) -Gp-(1 | 5% |
| 3) -Gp-(1 6) | 92% |
| -Gp-(1 3) | — |

It is therefore evident that the insoluble glucan is not an α-(1→6) linked dextran, but rather a glucan with a preponderance of α-(1→3) links. The insolubility in water is a consequence of the high content of α-(1→3) links, and not an effect of a high molecular weight or pronounced branching, as was previously assumed (Gibbons and Nygaard, Arch. oral Biol. 13, 1244-1262, 1968). For predominately α-(1→3) linked glucans of streptococcal origin the name mutan is suggested.

Furthermore, it is obvious that purified dextranases (E.C. 3.2.1.11.α-1,6-glucan 6-glucanohydrolase) are not capable of hydrolizing and solubilizing glucans of the mutan type, because of deficient enzyme-substrate specifity. Dextranases of normal commercial quality produced by a variety of strains of the genus Penicillium contain traces of an α-1,3-glucan 3-glucanohydrolase. For the sake of brevity the new enzyme will henceforth be referred to as mutanase. The two enzymes can be characterized after a separation by electrofocusing. As starting material, a commercial available dextranase (e.g., dextranase S, Schweiz. Ferment AG, Basel, Switzerland) may be used.

Some properties of the two enzymes are compiled in the following table.

| Property | Mutanase | Dextranase |
|---|---|---|
| Isoelectric point | 4.17 | 4.64 |
| Optimal activity at pH | 4.5* | 4.5** |
| Optimal activity at temperature °C. | 46* | 50** |
| Activity dependent on the presence of metal ions | not | not |

*4 hour incubation
**1 hour incubation

Both enzymes exhibit properties typical for many carbohydrases, but are clearly distinguished by the quantitative analyses of the end products of their enzymatic action on suitable substrates. The end products were analyzed with gas liquid chromatography after a 12 hour incubation period. The results are presented in the following tables.

Analyses of end products after incubation of mutan with purified mutanase from *Penicillium funiculosum* (N=6)

| End Product | Mol % ± S |
|---|---|
| α β-Glucose | 44.45 ± 1.04 |
| 1,3 Isomaltose | 40.2 ± 0.5 |
| 1,3 Isomaltotriose | 6.63 ± 0.15 |
| 1,3 Isomaltotetraose | 7.13 ± 0.63 |

Analyses of end products after incubation of dextran (Fluka, MW 80'000) with purified dextranase from *Penicillium funiculosum* (N=6)

| End product | Mol % ± S |
|---|---|
| α β-Glucose | 16.19 ± 1.05 |
| 1,6 Isomaltose | 67.73 ± 1.28 |
| 1,6 Isomaltotetraose | 13.30 ± 1.75 |

In dextrans synthesized by bacteria of the genus Leuconostoc, up to 35% α-(1→3) links may be found (Stacey and Barker in Polysaccharides of Microorganisms, Calderon Press, Oxford, p. 141, 1960). In general, this percentage is much lower in dextrans which are used for the production of the enzyme dextranase. Nevertheless, direct observation indicates that induction of the traces of mutanase is due to the small amounts of α-(1→3) links present in insoluble dextrans. On the other hand, the few α-(1→6) links present in mutan are sufficient to induce a small amount of dextranase when native mutan is used as carbon source for the production of mutanase with molds of the genus Penicillium.

By periodate oxidation followed by reduction with sodium borohydride these α-(1→6) links can be destroyed (Goldstein et al. in: Methods in Carbohydrate Chemistry, Vol. V., General Polysaccharides, Academic Press, New York/London, p. 361-370, 1965). If such a modified mutan, deprived of all α-(1→6) linked glucopyranose rings, is used as sole carbon source for the production of mutanase with strains of Penicillium such as *Penicillium lilacinum* NRRL 1896, *Penicillium funiculosum* NRRL 1768, NRRL 1132, or *Penicillium melinii* NRRL 1931, the culture filtrate will contain only mutanase and no dextranase.

Native mutan may be used for the production of mutanase when a strain of *Trichoderma harzianum* OMZ 779 is chosen for the synthesis of mutanase. This strain does not appear capable of synthesizing dextranase.

The strain has been deposited at the Central Bureau voor Schimmelcultures Baarn (Netherlands) CBS 243.71. The mutanase of this strain was purified by ammonium sulfate and acetone precipitation followed by chromatography on Sephadex G 150 and electrofocusing. The characteristics of this enzyme are distinctly different from the mutanases synthesized by strains of Penicillium, as may be observed in the following table:

Properties of mutanase isolated from Trichoderma harzianum OMZ 797, CBS 243.71.

| Properties | Mutanase from *Trichoderma harzianum* OMZ 797, CBS 243.71 |
|---|---|
| Isoelectric point at | |
| Major activity | 7.1 |
| Minor activity | 6.6 |
| Optimal temperature | 48° C. |
| Optimal activity at pH | 5.5 |
| Optimal stability at pH | 5.5 |
| Activity dependent on the presence of metal ions | no |

The pH-optima and pH-stabilities of mutanases isolated from *Penicillium funiculosum* NRRL 1178, *Penicillium lilacinum* NRRL 896 and *Trichoderma harzianum* CBS 243.71 were compared and presented in FIGS. 1 and 2 of the attached drawing.

The three mutanases have both different pH-optima and pH-stabilities when compared under identical conditions.

The end products of enzymatic activity of mutanase produced by *Trichoderma harzianum* CBS 243.71 after incubation for 12 hours with 6 mg mutan or modified mutan, are summarized in the following table:

|  | Mutanase Ip 6.6 | | Mutanase Ip 7.1 | |
|---|---|---|---|---|
|  | Mutan | mod. Mutan | Mutan | mod. Mutan |
| Released red sugars calculated as glucose mg | 3.63 | 3.09 | 5.24 | 4.82 |
| End products Mol % | | | | |
| Glucose | 90.31 | 87.23 | 83.98 | 85.4 |
| 1,6 Isomaltose | 8.24 | 0.19 | 0.33 | 0.23 |
| 1,3 Isomaltose | — | 6.71 | 13.08 | 9.54 |
| 1,3 Isomaltotriose | — | 2.01 | — | 0.92 |
| 1,6 Isomaltotriose | — | — | — | — |
| not identified | 1.45 | 3.84 | 2.61 | 3.90 |

The figures in this table demonstrate that mutanase from *Trichoderma harzianum* is highly specific for the α-(1→3) linked mutan and does not hydrolyze the α-(1→6) linked dextran. Between the two enzyme fractions having different isoelectric points, only slight differences are detectable in the composition of the resulting end product.

When the activity of mutanases produced by strains of the genus Penicillium is compared with the mutanase isolated from *Trichoderma harzianum* under substrate limiting conditions it is evident that the enzyme of the latter strain possesses the more powerful hydrolytic properties. The results of such an experiment are presented graphically in FIG. 3 of the attached drawing.

Thus mutanase appears to be an entire class of enzymes whose only point of commonality is their ability to attack the alpha 1,3 linked polysaccharides present in plaque. In like fashion, mutan may be a class of glucans having different degrees of water insolubility. The insolubility is a direct sequel to the content of alpha 1,3 links and the plaque matrix contains a series of such glucans with varying amounts of this critical linkage. Mutan is largely, e.g. at least 50%, alpha 1,3 linked.

Mutan appears to be unusually refractory. Enzymes capable of splitting alpha 1,3 glucosidic bonds have been described heretofore. However, the substrates for these enzymes were derived from fungal cell walls primarily, not from streptococci. These enzymes are not active on mutan. For example, Hasegawa et al in Journal of Biol Chem., Vol. 244, 5460–5470, 1969, described an endo-α-D-(1→3)-glucanase prepared from *Trichoderma viride*. However, their glucanase is not able to break down mutan, whereas mutanase can break down pseudonigeran. Furthermore, the microorganism used by Hasegawa does not produce mutanase, even if mutan is used as a part of the carbon source instead of pseudonigeran. However, mutanase and such enzymes might, nontheless, be identified by the same systematic name i.e. alpha 1,3 glucan-3-glucanohydrolase. For that reason the coined term mutanase is employed for identification of the enzymes of this invention, and the term mutan is more exactly defined as the class of microorganism produced glucans having more than 50% alpha 1,3 glucosidic bonds.

Initial screening studies for a mutanase producing microorganism may, of course, be made with all sorts of microorganism containing material, using for the substrate and carbon source plaque collected from dental scrapings. More convenient even for screening, let alone for large scale production, is the mutan which can be expressly produced by cultivation of a mutan producing microorganism. Specifically, the mutan may be synthesized by cultivating a bacterium of the genus *Streptococcus mutans* or *Streptococcus sanguis* and, in particular, the *Streptococcus mutans* strain CBS 350.71 identifiable as OMZ 176, then removing the cells from the fermented liquid, thereafter adding sucrose (in solution) to the cell-free fermented liquid. After a suitable incubation period the mutan may be filtered off and recovered. Desirably, the recovered mutan may be further treated to destroy the alpha 1,6 glucosidic bonds by periodate oxidation, followed by reduction leaving behind a mutan which contains exclusively or almost exclusively alpha 1,3 glucosidic bonds.

An important aspect of the present invention is production of mutanase by a microbiologic method from mutanase producing microorganisms using the synthetic mutan as the predominant carbon source. The cultivation may be carried out in conventional fashion at a pH between about a pH 2 and a pH 9 and at a temperature between about 10° C. and 45° C. The mutanase is recovered from the fermentation broth.

Mutanase producing microorganisms already found are: *Trichoderma harzianum, Penicillium lilacinum, Penicillium funiculosum, Penicillium melinii* (Qm 1931) and *Penicillium janthinellum*. The deposited microorganisms: *Trichoderma harzianum* CBS 243.71, *Penicillium lilacinum* NRRL 836 and CBS 595.71; *Penicillium funiculosum* NRRL 1132; NRRL 1768; and *Penicillium janthinellum* CBS 351.71.

As should be apparent from the above description, the mutanase can be dispersed in a non-toxic carrier (e.g. water) and compounded into an orally ingestible composition for treatment of plaque on living teeth. Desirably the oral composition or agent is substantially non-consumable, being for example, chewing gum. Other oral preparations such as toothpaste, mouth rinse, mouth spray are contemplated. In addition, the oral agent may be a consumable, as for example a chocolate preparation, any drink, candy drops. Preferred are long lasting agents such as candy drops or chewing gum because such agents remain in the mouth for extended periods of time, can be compounded to release enzymes gradually, and thereby allow the enzyme a substantial period of time for attacking the dental plaque.

A related use for mutanase is treatment of artificial teeth. Plaque forms on artificial teeth too and mutanase may be employed for removing plaque deposits therefrom. For such purposes the mutanase may be compounded in a soaking or cleansing composition.

Polysaccharides of the mutan type can be encountered in industry as well, as for example in piping or storage vessels which handle aqueous sugar solutions, e.g. molasses, when the equipment has become contaminated with polysaccharide producing microorganisms. For this purpose also the mutanase may be compounded in soaking or cleansing compositions.

The mutanase containing compositions contemplated according to practice of the present invention such as, for example, the oral agents, should contain enough mutanase to exhibit an activity of between 0.02 and 1000 mutanase units per gram of the composition, more often between 0.1 and 500 mutanase units per gram of the composition. A preferred range is from 0.2–100 mutanase units per gram of the composition. The mutanase containing compositions may, of course, have therein other enzymes, such as for example, dextranase, lipase, protease. Test work on isolated insoluble dental plaque matrix materials have indicated that complete solubilization thereof is dependent also on a non-carbohydrate moiety and that some lipase and protease activity can be beneficial for solubilization.

EXAMPLE A

The mutan may be prepared by cultivating *Streptococcus mutans* OMZ 176 (CBS No. 350.71) in brain-heart infusion (Difco) for 12 hours and by inoculating this broth in a fermentor containing a substrate of the following composition:

| | |
|---|---|
| Dialyzable parts of Bacto Tryptose | 30 g/l |
| Dialyzable parts of Bacto Yeast Extract | 15 g/l |
| Bacto-Casamino Acids | 7.5 g/l |
| K$_2$HPO$_4$ | 12 g/l |
| Glucose | |

The pH of this culture liquid is maintained automatically at 6.0, and a gas mixture consisting of 95% N$_2$ and 5% CO$_2$ is introduced in the broth at a flow rate of 0.3 l/min. When the acid production stops (approx. 16 hours after the beginning of fermentation), the cells are removed by centrifugation, and 5% sucrose is added to the cell-free fermented liquid. After incubation for 12 hours, the mutan is filtered off, washed with water, dialyzed against running tap water, and lyophilized. The yield is 5 g/l.

EXAMPLE 1

Production of mutanase with Trichoderma OMZ 779, CBS 243.71

A salt according to Mandels, et al., J. Bact. 83, 400–408, 1962, solution with a shake flask is inoculated with the above mentioned strain and shaken for 96 hours, whereby the carbon source consists of 0.2% glucose and 0.2% mutan (produced as in Example A). This culture liquid is inoculated to a fermentor with the same substrate. Air is introduced with a flow of 1 liter air per minute and per liter culture liquid. The temperature of the culture liquid is 28° C., and the rotational velocity of the stirrer is 300 rpm. The pH is automatically adjusted to 6.0. After 160 hours of cultivation, the mutanase activity is 2.5 units/ml culture liquid; the dextranase activity is less than 0.02 dextranase units/ml culture liquid.

EXAMPLE 2

In this example, a mutan, the alpha 1,6 bonds of which are broken down, is used. For this purpose mutan produced according to Example A is oxidized in a solution of periodate (4 mol periodate per mol anhydroglucose). The molarity of periodate is kept below 0.5. The oxidation is carried out 144 hours in the dark at 4° C. The mutan is centrifuged off and dialyzed against running tap water over night. The reduction is carried out at room temperature in an aqueous solution of sodium borohydride (2 g sodium borohydride per g mutan). 24 hours later the mixture is neutralized with 32% HCl. The thus modified mutan is washed and lyophilized.

The production of mutanase is carried out as in Example 1 with two exceptions: Instead of mutan used in Example 1, the modified mutan is used and instead of the fungus Trichoderma harzianum CBS No. 243.71, Penicillium lilacinum NRRL 896 is used for the cultivation. After 184 hours of cultivation a yield of 0.26 mutanase units/ml culture filtrate is obtained. The dextranase activity is less than 0.02 dextranase units/ml culture filtrate.

In order to show the mutan-degrading ability of the mutanase prepared according to the invention, the mutanase produced as above and then purified by isoelectric focusing is tested on an agar plate prepared as follows: 45 mg mutan, 225 mg agar and 15 ml 0.2 N acetate buffer with pH 5.0, stirred and heated to boiling, then poured into a Petri dish. After solidification some holes are drilled in the mutan-containing agar plate. The holes are filled with purified mutanase, activity about 2 mutanase units (0.03 ml), and the plates are incubated over night at 37° C. The mutan in the vicinity of the holes is completely hydrolyzed. Purified dextranase in a concentration of 200 dextranase units per ml does not show any degrading effect on the mutan whatsoever.

EXAMPLE 3

In order to show the mutan-degrading ability of the mutanase prepared according to the invention, 50 mg lyophilized plaque collected from school children was suspended in 100 ml H$_2$O means of ultrasonic power. The material was centrifuged and the extraction of the sediment repeated twice with volumes of 10 ml double distilled water. The soluble fraction was discarded. The insoluble residue (38.5 mg) was suspended in 10 ml acetate buffer and heated to boiling. 1 ml of the plaque suspension was incubated for 4 hours with 1 ml purified mutanase (Penicillium funiculosum), the activity of which was 2.2 mutanase units. The quanitative mutanase activity determinations were carried out according to Tsuchiya et al. (J. Bacteriol. 64, 513–519, 1952), using mutan instead of dextran at pH 5.5. Activity units are defined accordingly, but refer to mutan and not to dextran as substrate.

The quantity of the released reducing sugars were determined colorimetrically. The mutanase was able to release 0.12 mg reducing sugar, determined as glucose. A control with purified dextranase instead of mutanase (240 dextranase units per ml) did not show any release of reducing sugar whatsoever.

In a second experiment a polysaccharide-containing fraction of dental plaque was extracted from the water-insoluble portion using 1 n KOH. The material was precipitated with 45% ethanol, washed with water, lyophilized and 5.0 mg of this material was suspended in 5 ml of acetate buffer pH 5.5. To this suspension 2 mg (4.6 MU) of lyophilized mutanase from Trichoderma harzianum were added. The sample was incubated at 40° C. overnight. After incubation the suspended particles were completely dissolved. A total of 0.65 mg of reducing sugar, calculated to be glucose, was released.

EXAMPLE 4

Addition of mutanase to various consumable products

(a) Food

Mutanase may be added to all kinds of processed food in concentrations of 0.02–1000 units per gram of composition, especially to foods containing sucrose, such as chocolate cereals, toffees, sweets, bisquits, etc.

Formation of dental plaque is inhibited by addition of this enzyme. Mutanase is distributed in the oral cavity during mastication.

(b) Beverages

Mutanase may also be added to all kinds of beverages in concentrations between 0.02–1000 units per ml, especially to drinks and juices containing sucrose. Formation of extracellular mutan will be prevented if this enzyme is supplied to the teeth during drinking.

(c) Chewing Gum

Mutanase may be added to chewing gum in formulations described in textbooks or generally sold on the market—in concentrations between 0.02–1000 units per gram composition. This carrier would guarantee a prolonged contact of the enzyme with teeth and gums during chewing.

EXAMPLE 5

Addition of mutanase to nonconsumable oral agents

(a) Toothpaste, gels, powder

Accepted formulations as described in textbooks or sold on the market are supplemented with 0.02–1000 units mutanase per gram of the formulation. These products are to be used in the normal manner on a toothbrush; gel may be applied with an intraoral tray.

(b) Mouthwash, solutions

To mouthwashes or solutions of the kind described in textbooks or found on the market 0.02–1000 units mutanase per ml may be added. These products are used for normal rinsing, for topical application on teeth and gums or to clean dentures by soaking.

What is claimed is:

1. A fermentation process for producing an enzyme capable of selectively attacking a streptococci derived alpha-1,3 glucosidic bonded glucan which comprises oxidizing and reducing a streptococci derived dental plaque glucan characterized by at least 50% alpha-1,3 glucosidic bonds to destroy the alpha-1,6 bonds therein, leaving a glucan which contains almost exclusively alpha-1,3 glucosidic bonds, aerobically cultivating a microorganism thereon, and thereafter recovering the enzyme produced extracellularly by the microorganism from the fermentation broth.

2. An enzyme capable of hydrolyzing the streptococci derived dental plaque glucan having a majority of $\alpha 1 \rightarrow 3$ glucosidic bonds.

3. A dental treating composition comprising a dental treating carrier and an effective amount of an enzyme capable of hydrolyzing the streptococci derived dental plaque glucan having a majority of $\alpha 1 \rightarrow 3$ glucosidic bonds.

4. A method of treating teeth comprising subjecting teeth to a dental treating composition comprising a dental treating carrier and an effective amount of an enzyme capable of hydrolyzing the streptococci derived dental plaque glucan having a majority of $\alpha 1 \rightarrow 3$ glucosidic bonds.

5. A fermentation process for producing an enzyme capable of hydrolyzing a streptococci derived dental plaque glucan having a majority of $\alpha$-$(1 \rightarrow 3)$ glucosidic bonds which comprises cultivating a microorganism on a streptococci derived glucan having a majority of $\alpha$-$(1 \rightarrow 3)$ glucosidic bonds, said glucan being the predominant carbon source for the microorganism being cultivated thereon, then recovering the enzyme produced extracellularly by the microorganism from the fermentation broth.

6. The process of claim 5 wherein the said glucan is oxidized and reduced to destroy any alpha 1,6 bonds therein prior to use in said fermentation process.

7. The process of claim 5 wherein the said glucan is synthesized by aerobic cultivation of *Streptococcus mutans* OMZ 176 or natural or synthetic variants or mutants thereof.

8. The process of claim 5 wherein the microorganism is a member selected from the group consisting of *Trichoderma harzianum* CBS 243.71, *Penicillium lilacinum* NRRL 896 and CBS 595.71, *Penicillium funiculosum* NRRL 1132 and 1768, *Penicillium melinii* NRRL 1931, *Penicillium janthinellum* CBS 351.71 or natural or synthetic variants or mutants thereof.

* * * * *